United States Patent [19]

Kamiya et al.

[11] Patent Number: 5,136,373
[45] Date of Patent: Aug. 4, 1992

[54] IMAGE PROCESSING APPARATUS

[75] Inventors: Kiyoshi Kamiya; Eiji Inuzuka; Masahumi Oshiro; Shigeru Uchiyama; Koji Suzuki, all of Shizuoka, Japan

[73] Assignee: Hamamatsu Photonics K. K., Shizuoka, Japan

[21] Appl. No.: 638,027

[22] Filed: Jan. 7, 1991

Related U.S. Application Data

[63] Continuation of Ser. No. 540,602, Jun. 19, 1990, abandoned.

[30] Foreign Application Priority Data

Jun. 22, 1989 [JP] Japan ................... 1-160309

[51] Int. Cl.$^5$ .............................................. H04N 7/18
[52] U.S. Cl. ................................ 358/93; 358/101; 358/106; 358/211
[58] Field of Search ................... 358/93, 101, 106, 211, 358/225, 183; 382/8

[56] References Cited

U.S. PATENT DOCUMENTS

| | | | |
|---|---|---|---|
| 4,602,282 | 7/1986 | Kurono | 358/211 |
| 4,680,635 | 7/1987 | Khurana | 358/211 |
| 4,755,874 | 7/1988 | Esrig | 358/211 |
| 4,811,090 | 3/1989 | Khurana | 358/93 |

FOREIGN PATENT DOCUMENTS

| | | |
|---|---|---|
| 0164680 | 12/1985 | European Pat. Off. . |
| 60-02078 | 6/1985 | Japan . |
| 62-179067 | 6/1987 | Japan . |
| 2-31175 | 1/1990 | Japan . |

OTHER PUBLICATIONS

N. Khurana et al., "Analysis of Product Hot Electron Problems by Gated Emission Microscopy" CH2256-6/86/86/0000-0189$01.00, 1986 IEEE/IRPS pp. 189-194.

A. G. Chynoweth et al., "Photon Emission From Avalanche Breakdown in Silicon" Physical Review, vol. 102, No. 2, 4-15-56, pp. 369-375.

S. Tam et al., "Spatially Resolved Observation of Visible-Light Emission From Si MOSFET's" IEEE Electron Device Letters, vol. EDL-4, No. 10, Oct. 1983, pp. 386-388.

Akira Toriumi et al., "A Study of Photon Emission From n-Channel MOSFET's", IEEE Transactions on Electron Devices, vol. ED-34, No. 7, Jul. 1987, pp. 1501-1508.

Primary Examiner—Howard W. Britton
Attorney, Agent, or Firm—Finnegan, Henderson, Farabow, Garrett and Dunner

[57] ABSTRACT

Configuration image data representing an external form of an object is stored in advance in a configuration image memory. A two-dimensional image of faint light emitted from the object is detected by a high-sensitivity image pickup means including a two-dimensional photon-counting tube. Faint light image data representing the detected faint light image is accumulated by an adder circuit, and stored in a faint light image memory. The stored faint light image data is superposed on the stored configuration data for each accumulating operation, and based on the superposed image data a superposed image is successivley displayed on a display device.

7 Claims, 1 Drawing Sheet

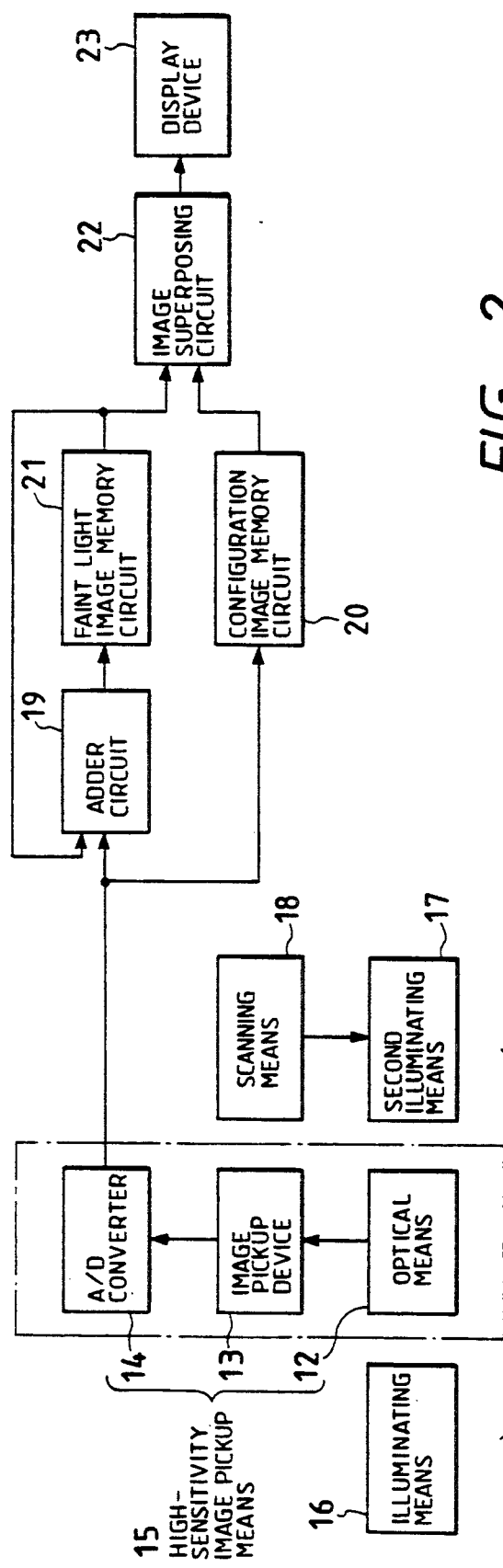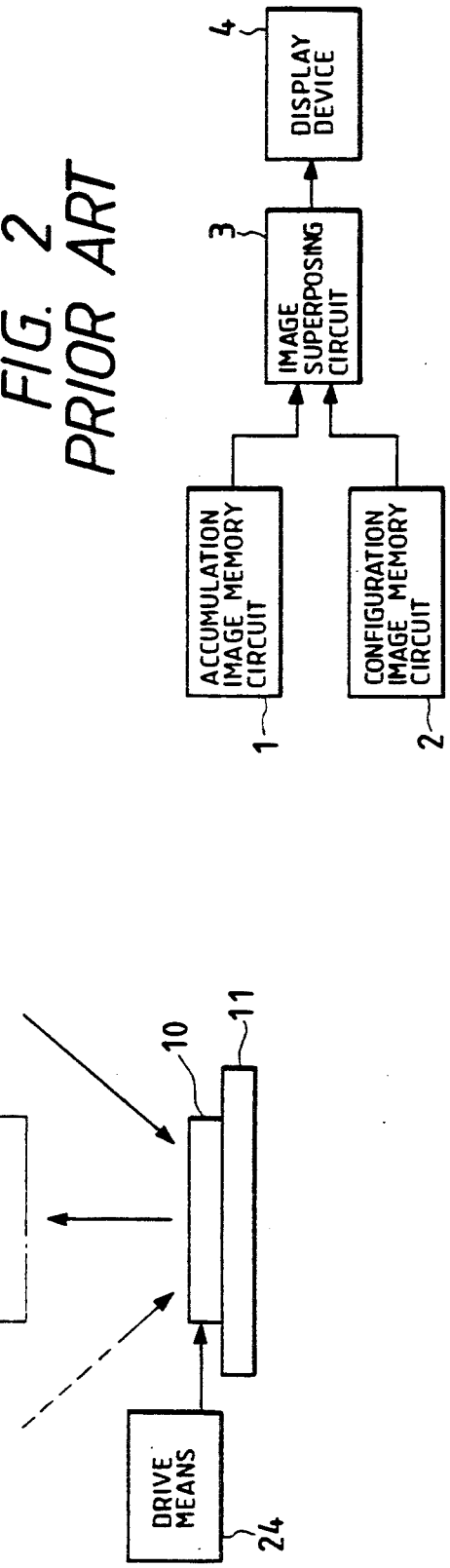

IMAGE PROCESSING APPARATUS

This application is a continuation of application Ser. No. 07/540,602 filed Jun. 19, 1990, now abandoned.

BACKGROUND OF THE INVENTION

The present invention relates to an image processing apparatus for displaying an accumulated image of very faint light emitted from an object and an image of a configuration of the object in an overlay fashion.

In recent field-effect transistors (FETs) having small gate length, carriers (electrons or holes) may be accelerated by a strong electric field to such an extent that the internal recombination of the carriers occurs to cause emission of a photon. Carriers in such a state are called "hot carriers". There are some papers reporting the detection of light emission by the hot carriers, though it is very weak.

It is also known that very faint light is emitted in the process of dielectric breakdown of an oxide film. In recent MOS integrated circuits, a voltage of typically 3 V or 5 V is applied across a gate oxide thin film of several hundreds angstroms in thickness. Therefore, the resultant high electric field across the gate oxide film, which reaches several megavolts/cm, may cause dielectric breakdown of the gate oxide thin film very faint light is emitted in the breakdown process.

To locate a faint light emitting point in the object, it is necessary to obtain a combined image in which an accumulated image of the faint light is displayed over an image of a configuration of the object. To this end, an image processing apparatus as shown in FIG. 2 has conventionally been used. Faint light emitted from a faint light emitting object, which ranges from visible light to infrared light, is imaged on an image intensifier by an optical microscope. The formed image is then converted into a television signal by a television camera. The image data thus obtained is accumulated over a long period of time by an accumulation image memory circuit 1, and the accumulated image data is stored therein. The object is externally illuminated to gather image data of the object configuration, and the resultant image data is stored into a configuration image memory circuit 2. The accumulation image data and the configuration image data are superposed on each other by an image superposing circuit, 3, and the superposed image is displayed in an overlay fashion by a display device 4.

Thus, in the conventional image processing apparatus, the faint light image and the configuration image are stored in separate memory circuits in advance at different times, and thereafter the two images are superposed on each other. Therefore, it is impossible to observe a light emitting process of the faint light and a light emitting location in the object in real time. Further, it takes much time to obtain the superposed image.

SUMMARY OF THE INVENTION

Accordingly, an object of the present invention is to provide an image processing apparatus which allows one to observe a light emitting process of very faint light and a light emitting location in the object in real time.

According to the invention, an image processing apparatus comprises:

high-sensitivity image pickup means for picking up, as a two-dimensional pattern, an image of faint light emitted from an object to produce digital faint light image data, and picking up an image of light reflected by the object being illuminated by external illuminating means to produce configuration image data representing an external form of the object;

digital integration accumulating means for integrating and storing the digital faint light image data;

configuration image memory means for storing the configuration image data;

image superposing means for superposing, for each accumulating operation in the accumulating means, the accumulated faint light image data on the configuration image data from the configuration image memory means; and display means for successively displaying a superposed image of the faint light image and the configuration image based on the superposed image data from the image superposing means.

With such an arrangement, the faint light emitting object is illuminated by the external illuminating means, and sensitivity of the high-sensitivity image pickup means is lowered. Under this condition, the high-sensitivity image pickup means produces the configuration image data of the object. The configuration image data thus obtained is stored in the configuration image memory means. Even if the configuration image data is applied to the accumulation means, it is not stored in the faint light image memory means. Then, the external illuminating means is turned off, and the sensitivity of the high-sensitivity image pickup means is adjusted to its highest sensitivity so that it can operate in the photon-counting mode. The faint light emitted from the object is picked up by the high-sensitivity image pickup means, in which the image pickup means counts photons one by one in a two-dimensional manner, thereby to detect the faint light image as a two-dimensional pattern. The faint light image data is accumulated by and stored in the accumulating means. The faint light image data thus accumulated and the stored configuration image data are superposed on each other in the image superposing means, and the superposed image is successively displayed in the display device based on the superposed image data. One can observe the faint light image which progressively changes while being accumulated, and can identify a location of the object where emission of the faint light occurs, in a real time manner.

BRIEF DESCRIPTION OF THE DRAWINGS

FIG. 1 is a block diagram showing an embodiment of an image processing apparatus according to the present invention; and FIG. 2 is a block diagram showing a conventional image processing apparatus.

DETAILED DESCRIPTION OF THE PREFERRED EMBODIMENT

An embodiment of an image processing apparatus according to the present invention will be described with reference to FIG. 1.

A faint light emitting object 10 is, for example, a semiconductor device, to which a driving power or driving signals are supplied from an external drive means 24. Under a strong internal electric field, hot carriers are converted into photons, i.e., very faint light. The object 10 may be of any other type whose light emitting mechanism is different from the above one. The object 10 is placed on a table 11 which is movable to an inspection position. An optical means 12 is provided adjacent to the object 10. The optical means includes an optical microscope for collecting very faint light emitted from the object 10, a macro lens, etc. A photocathode of an image pickup device 13 for converting an optical signal into an electrical signal is provided in an image forming plane of the optical means 12. The image pickup device 13 may be a so-called two-dimensional photon-counting tube which two-dimensionally detects light in terms of a photon as a quantum of light (one photon by one photon). The sensitivity of the two-dimensional photon-counting tube is adjusted such that reflected light from the object 10 under illumination is detected at lower sensitivity and very faint light emitted from the object 10 is detected at higher sensitivity. The image pickup device 13 is coupled at the output with an A/D converter 14 for converting the analog electrical signal to a digital signal. The optical means 12, the image pickup device 13 and the A/D converter 14 make up a high-sensitivity image pickup means 15. An illuminating means 16 is located adjacent to the object 10, and is used when image data of a configuration (external form) of the object 10 is produced. If desired, there may be provided another illuminating means 17 for illuminating the object 10 with a light beam of a specific wavelength, and a scanning means 18 for effecting the scanning by the light beam of the specific wavelength, to analyze light emitted from the object 10 in response to the illumination by the second illuminating means 17.

The high-sensitivity image pickup means 15 is coupled at the output with both of an adder circuit 19 and a configuration image memory circuit 20. The adder circuit 19 is coupled with a faint light image memory circuit 21. The output of the memory circuit 21 is fed back to the input side of the adder circuit 19. Both the memory circuits 21 and 22 are connected to an image data superposing circuit 22, which is then connected to a display device 23.

In operation, the faint light emitting object 10 is first illuminated by the illuminating means 16. Light reflected from the object 10 is processed by the high-sensitivity image pickup means 15; first, the light is collected by the optical means 12 and imaged on the image pickup device 13 whose sensitivity is lowered in this mode, and then the analog signal output from the image pickup device 13 is converted into a digital signal as configuration image data by the A/D converter 14.

This configuration image data is stored into the configuration image memory circuit 20. The same data is also transferred to the adder circuit 19, but is not stored in the faint light image memory circuit 21.

After gathering of the configuration image data is completed, the illuminating means 16 is turned off, and the image pickup means 15 operates to detect very faint light from the object 10. In this mode of detecting the very faint light, the sensitivity of the image pickup device 13 is adjusted to its highest condition. The faint light thus detected is also subjected to the A/D conversion, and the converted signal is applied through the adder circuit 19 to the faint light image memory circuit 21. The stored data is fed back to the adder circuit 19, and is added to the subsequent faint image data. The faint light image data resulting from such repeated addition is transferred, together with the configuration image data, to the image data superposing circuit 22 every time the addition is performed. The two image data are superposed on each other in the image data superposing circuit 22. The display device 23 displays the superposed image and an accumulating process of the faint light image in real time.

As seen from the foregoing description, an accumulating process of a faint light image from a faint light emitting object can be displayed together with a configuration image of the object in an overlay fashion. Accordingly, one can observe in real time a location in the object where very faint light is being emitted, and a process of the light emission.

In a defect, analysis of semiconductor devices, for example, a very faint light emission by hot carriers or a light emission due to dielectric breakdown of a gate oxide film is additively displayed being overlaid on a pattern image of an IC. By carefully observing such dynamic overlay images, it is possible to quickly recognize a light emitting process and to identify a light emitting location or defective location of the device. In another application to biology, when white blood cells capture bacteria and react with luminol added to an external liquid, active oxygen is emitted. The very weak light which is emitted during the process is additively displayed on a configuration image as previously obtained by illuminating an object. In such a manner, how white blood cells capture bacteria can be observed in real time.

What is claimed is:

1. An image processing apparatus comprising:
   high-sensitivity image pickup means for picking up, as a two-dimensional pattern, an image of faint light emitted from an object to produce digital faint light image data, and picking up an image of light reflected by the object being illuminated by external illuminating means to produce configuration image data representing an external form of the object;
   digital integration means for integrating and storing the digital faint light image data;
   configuration image memory means for storing the configuration image data;
   image superposing means for superposing, for each accumulating operation in the accumulating means, the accumulated faint light image data on the configuration image data from the configuration image memory means; and
   display means for successively displaying a superposed image of the faint light image and the configuration image based on the superposed image data from the image superposing means.

2. The apparatus according to claim 1, wherein the digital integration means comprises an adder means for adding input faint light image data to preceding faint light image data, and faint light image memory means for storing the added faint light image data and feeding back the stored faint light image data to the adder means as the preceding faint light image data.

3. The apparatus according to claim 1, wherein the image pickup means is adjustable and is adjusted to low-sensitivity for bright light levels and is further adjusted to high-sensitivity for dim light, said apparatus further comprising means for positioning the object with respect to the high-sensitivity image pickup means.

4. The apparatus according to claim 1, further comprising second illuminating means for scanning the object with illumination light having a predetermined wavelength.

5. The apparatus according to claim 1, wherein the object is a semiconductor device emitting the faint light caused by recombination of hot carriers.

6. The apparatus according to claim 1, wherein the high-sensitivity image pickup means is adjustable according to light level and comprises optical means for collecting light from the object and forming an image of the collected light, a two-dimensional photon-counting tube for detecting the formed image as the two-dimensional pattern and producing an analog electrical signal representing the detected image, and an A/D converter for converting the analog electrical signal to a digital signal as the faint light image data or the configuration image data.

7. The apparatus according to claim 6, wherein the optical means comprises an optical microscope and macro lens.

* * * * *